United States Patent [19]

Cossement et al.

[11] Patent Number: 4,956,367
[45] Date of Patent: Sep. 11, 1990

[54] 2-AMINO-4-MORPHOLINO-6-PROPYL-1,3,5-TRIAZINES

[75] Inventors: Eric Cossement; Jean Gobert; Roland Boydens; Jacques Mathieu, all of Brussels, Belgium

[73] Assignee: U C B S.A., Brussels, Belgium

[21] Appl. No.: 390,878

[22] Filed: Aug. 8, 1989

[30] Foreign Application Priority Data

Aug. 16, 1988 [GB] United Kingdom ............... 8819493

[51] Int. Cl.$^5$ ............... C07D 413/14; C07D 413/04; A61K 31/53; A61K 31/535
[52] U.S. Cl. ............... 514/236.2; 544/113; 540/598; 514/212
[58] Field of Search ............... 544/113; 514/236.2, 514/212; 540/598

[56] References Cited

U.S. PATENT DOCUMENTS 3,549,755 12/1970 Kodama et al. ............ 424/248

FOREIGN PATENT DOCUMENTS 2226474 2/1973 Fed. Rep. of Germany .
2262512 9/1975 France .
49-69688 7/1974 Japan .

OTHER PUBLICATIONS

Wakabayashi et al., Chemical Abstracts, vol. 72 (1970) No. 100653v.

Primary Examiner—John M. Ford
Attorney, Agent, or Firm—Wenderoth, Lind & Ponack

[57] ABSTRACT

New 2-amino-4-morpholino-6-propyl-1,3,5-triazines having the formula

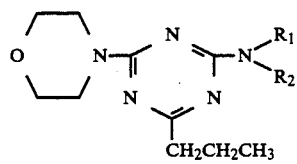

(I)

wherein
$R_1$ is hydrogen, alkyl, aralkyl or acetyl,
$R_2$ is hydroxyl, hydroxyalkyl, alkoxyalkyl, dialkylamino, arylhydroxyalkyl, (hydroxy-cycloalkyl)alkyl, alkanoyloxyalkyl, benzoyloxyalkyl, phenylacetyloxyalkyl, aminocarbonyloxyalkyl, $COR_3$ or $CONR_4R_5$, or
$NR_1R_2$=(hydroxyalkyl)alkyleneimino,
$R_3$=alkyl, aryl, haloaryl, alkylaryl, alkoxyaryl, aralkyl or aryloxy,
$R_4$=$R_5$=hydrogen or alkyl, alkyl, alkoxy and alkanoyloxy having 1 to 4 carbon atoms, cycloalkyl and alkyleneimino having 4 to 6 carbon atoms. Moreover, when $R_1$ is acetyl, $R_2$ is acetoxyalkyl.

Processes for the preparation thereof and pharmaceutical compositions containing the same are also given. In particular, these compounds are useful for the treatment of cognitive and behavioral disorders associated with aging and dementia syndromes, e.g. those associated with Alzheimer's disease.

12 Claims, No Drawings

2-AMINO-4-MORPHOLINO-6-PROPYL-1,3,5-TRIAZINES

The present invention relates to new 2-amino-4-morpholino-6-propyl-1,3,5-triazines and the non-toxic, pharmaceutically acceptable acid addition salts thereof, as well as to processes for the preparation thereof. It also relates to pharmaceutical compositions containing these new compounds.

2-Amino-1,3,5-triazines which are substituted in the 4-position by an amino group, an amino group which is mono- or disubstituted by an alkyl, alkenyl, cycloalkyl, aryl or aralkyl radical, or by a nitrogen-containing heterocyclic radical, and in the 6-position by an alkyl, aryl or aralkyl radical are already known from Japanese patent application No. 69688/74. In particular, the preparation of 2-amino-4-morpholino-6-propyl-1,3,5-triazine is described therein. According to this patent application, these compounds have the property of increasing the secretion of corticoids and in particular glucocorticoids.

K. WAKABAYASHI et al. (Yuki Gosei Kagaku Kyokai Shi,28,(1970),252–260; Chem.Abstr.72,(1970),100653v) have moreover synthesized 2-alkyl-4,6-bis(alkylamino)-1,3,5-triazines in which the radical in the 2-position contains 1 to 17 carbon atoms and can also represent the trichloromethyl, tribromomethyl or 2-chloroethyl group, whilst the radicals in the 4- and 6- position are identical and can be substituted by a hydroxyl group, or represent a nitrogen-containing heterocyclic radical, such as the piperidino or morpholino radical. A representative compound of this family is 2-methyl-4,6-dimorpholino-1,3,5-triazine. These compounds have been studied for their herbicidal activity and for their property of inhibiting the transformation of ammonia into nitrate. However, pharmacological properties are not mentioned therein.

We have now found new 2-amino-4-morpholino-6-propyl-1,3,5-triazines which have valuable pharmaceutical properties and in particular the property of potentiating the central and peripheral cholinergic effects caused by a cholinometic agent such as, for example, oxotremorine, even though these compounds do not have a cholinergic effect of their own. Moreover, it has also been found that these compounds have the advantageous property of attenuating the effects resulting from cholinergic hypofunction induced by a cholinergic antagonist such as, for example, scopolamine. The cholinergic system is widely involved in the phenomena of memorization and learning. Thus, for example, administration of an anticholinergic agent such as scopolamine to young subjects gives rise to memory deficiencies similar to those observed in elderly subjects. Conversely, cholinergic agents, such as physostigmine, are capable of combating the amnesia resulting from the administration of anticholinergic agents (S.D. GLICK et al., Behavioral Biology. (1972),245–254; U. SCHINDLER et al., Drug Develop.Res.4,(1984), 567–576). It is furthermore currently well-established that one of the characteristics most frequently associated with dementia is precisely an impairment of the cholinergic system (Cellular and molecular basis of cholinergic function, ed. M. J. DOWDALL & J. N. HAWTHORNE, 1987, chapter 99: art. by A. NORDBERG et al.) For this reason, these compounds can be used for the treatment of cognitive and behavioral disorders associated with ageing and with dementia syndromes. In particular, they are used in the treatment of disorders associated with Alzheimer's disease, with senile dementia, Alzheimer's type, and with any evolutive cognitive pathology (C. G. GOTTFRIES, Psychophsrmacology,86,(1985),245–252: C. G. GOTTFRIES, Neurobiology of Ageing,4,(1983),261–271).

More particularly, the present invention relates to new 2-amino-4-morpholino-6-propyl-1,3,5-triazines having the general formula

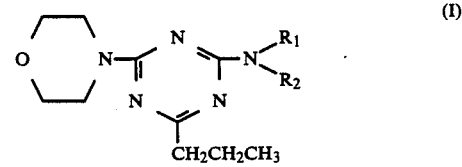

wherein $R_1$ represents a hydrogen atom, an alkyl, aralkyl or acetyl radical.

$R_2$ represents a hydroxyl group, a hydroxyalkyl, alkoxyalky dialkylamino, aryl-hydroxyalkyl, (hydroxycycloalkyl)alkyl, alkanoyloxyalkyl, benzoyloxyalkyl, phenylacetyloxyalkyl or aminocarbonyloxyalkyl radical, a $COR_3$ group in which $R_3$ represents an alkyl, aryl, haloaryl, alkylaryl, alkoxyaryl, aralkyl or aryloxy radical, or a $CONR_4R_5$ group in which $R_4$ and $R_5$ represent a hydrogen atom or an alkyl radical, or $R_1$ and $R_2$, together with the nitrogen atom to which they are attached, represent an alkyleneimino radical substituted by a hydroxyalkyl radical, the alkyl, alkoxy and alkanoyloxy radicals having 1 to 4 carbon atoms and the cycloalkyl and alkyleneimino radicals having 4 to 6 carbon atoms. with the proviso that when $R_1$ represents the acetyl radical, $R_2$ represents an acetoxyalkyl radical, and to the non-toxic pharmaceutically acceptable acid addition salts thereof.

As examples of the hydroxyalkyl radical there may be mentioned the 2-hydroxyethyl, 3-hydroxypropyl, 2-hydroxypropyl, 2-hydroxybutyl, 1-(hydroxymethyl)propyl, 2,3-dihydroxypropyl and 2-hydroxy-1,1-bis(hydroxymethyl)ethyl radicals and the like.

As an example of an aryl-hydroxyalkyl radical there may be mentioned the 2-hydroxy-1-(hydroxymethyl)-2-phenylethyl radical and the like.

As examples of the (hydroxy-cycloalkyl)alkyl radical there may be mentioned the (1-hydroxycyclohexyl)methyl) radical and the like.

As an example of the alkanoyloxyalkyl radical there may be mentioned the 2-(acetoxy)ethyl and 2-(isobutyryloxy)ethyl radicals and the like.

As an example of an alkyleneimino radical substituted by a hydroxyalkyl radical there may be mentioned the 2-hydroxymethyl-pyrrolidino and 2-hydroxymethyl-piperidino radicals and the like.

Preferred compounds according to the present invention are the 2-amino-4-morpholino-6-propyl-1,3,5-triazines of general formula I wherein $R_1$ represents a hydrogen atom or an alkyl radical, $R_2$ represents a hydroxyl group, a hydroxyalkyl, alkoxyalkyl dialkylamino or alkanoyloxyalkyl radical or a $COR_3$ group, in which $R_3$ represents an aryl radical which is unsubstituted or substituted by a halogen atom or an alkyl or alkoxy radical, the alkyl, alkoxy and alkanoyloxy radicals having 1 to 4 carbon atoms, and the non-toxic pharmaceutically acceptable acid addition salts thereof.

Particularly preferred compounds according to the invention include

2-[(4-morpholino-6-propyl-1,3,5-triazin-2-yl)amino]-ethanol, 2-(hydroxyamino)-4-morpholino-6-propyl-1,3,5-triazine, 2-[(2-methoxyethyl)amino]-4-morpholino-6-propyl-1,3,5-triazine, (S)-3-[(4-morpholino-6-propyl-1,3,5-triazin-2-yl)amino]-2-propanol, (R)-3-[(4-morpholino-6-propyl-1,3,5-triazin-2-yl amino]-2-propanol, 2-(2,2-dimethylhydrazino)-4-morpholino-6-propyl-1,3,5-triazine, N-(4-morpholino-6-propyl-1,3,5-triazin-2-yl)-benzamide hydrochloride, N-methyl-N-(4-morpholino-6-propyl-1,3,5-triazin-2-yl)-benzamide hydrochloride, 2-[[2-(acetoxy)ethyl]amino]-4-morpholino-6-propyl-1,3,5-triazine.

The present invention also relates to the non-toxic pharmaceutically acceptable acid addition salts of the 2-amino-4-morpholino-6-propyl-1,3,5-triazines of formula I. As examples of pharmaceutically acceptable acids there may be mentioned mineral acids, such as hydrochloric, hydrobromic, sulfuric, nitric and phosphoric acid and organic acids, such as acetic, citric, tartaric, benzoic, salicylic and maleic acid.

When the molecule contains an asymetric carbon atom, the compounds of formula I may be either in the form of a racemic mixture or in the form of one of the enantiomers. These various forms are also within the scope of the present invention.

The 2-amino-4-morpholino-6-propyl-1,3,5-triazines according to the present invention can be prepared by one of the following processes:

(a) When in formula I, $R_1$ represents a hydrogen atom, an alkyl or aralkyl radical and $R_2$ represents a hydroxyl group, a hydroxyalkyl, alkoxyalkyl, dialkylamino, aryl-hydroxyalkyl or (hydroxycycloalkyl)alkyl radical, or $R_1$ and $R_2$, together with the nitrogen atom to which they are attached, represent an alkyleneimino radical substituted by a hydroxyalkyl radical, 2-chloro-4-morpholino-6-propyl-1,3,5-triazine of the formula II is reacted with an amine of the formula $HNR_1R_2$ (III) according to the equation

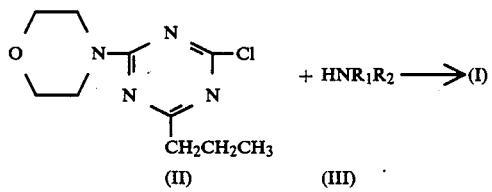

(II)  (III)

In these formulae, $R_1$ and $R_2$ have the meanings given above.

(b) When in formula I, $R_1$ represents a hydrogen atom, an alkyl or aralkyl radical and $R_2$ represents a hydroxyl group, a hydroxyalkyl, alkoxyalkyl, dialkylamino, aryl-hydroxyalkyl or (hydroxycycloalkyl)alkyl radical, or $R_1$ and $R_2$, together with the nitrogen atom to which they are attached, represent an alkyleneimino radical substituted by a hydroxyalkyl radical, a 2-amino-4-chloro-6-propyl-1,3,5-triazine of the formula IV is reacted with a morpholine of the formula V according to the equation

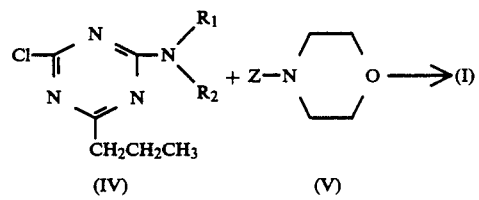

(IV)  (V)

In these formulae $R_1$ and $R_2$ have the meanings given above and Z represents a hydrogen atom or a methyl radical.

Processes (a) and (b) above are carried out at elevated temperature, generally at the boiling point of the solvent used, and in the presence of a base. The solvent in which these reactions are carried out is either the amine itself, used in excess, or an inert organic solvent, preferably dioxane, and in the latter case, the base used is an inorganic or organic base other than the amine used in the reaction, for example triethylamine.

The 2-chloro-4-morpholino-6-propyl-1,3,5-triazine (II) used as the starting compound is already known (T. TSUJIKAWA et al., Yakugaku Zasshi,95,(1975),5-12-520).

The starting compounds of the formula IV are prepared by conventional methods, by reacting 2,4-dichloro-6-propyl-1,3,5-triazine with an amine of the formula $HNR_1R_2$ (III), in which $R_1$ and $R_2$ have the meanings given above.

(c) When in formula I, $R_1$ represents a hydrogen atom, an alkyl or aralkyl radical and $R_2$ represents a $COR_3$ group, in which $R_3$ is an alkyl, aryl, haloaryl, alkylaryl, alkoxyaryl, aralkyl or aryloxy radical, the alkyl and alkoxy radicals having 1 to 4 carbon atoms, a 2-amino-4-morpholino-6-propyl-1,3,5-triazine of the formula VI is reacted, in equimolar proportions, with an $R_3$-carbonyl halide of the formula VII according to the equation

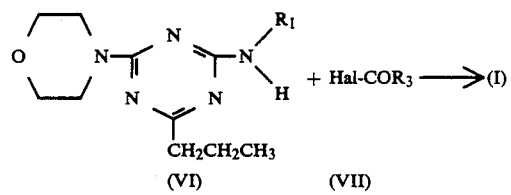

(VI)  (VII)

In these formulae, $R_1$ and $R_2$ have the meanings given above and Hal represents a halogen atom, preferably a chlorine atom. This reaction is known per se and is generally carried out in an organic solvent, such as, for example, dichloromethane, dichloroethane or pyridine, at a temperature between room temperature and the boiling point of the solvent and in the presence of an acid acceptor, such as a tertiary organic base (e.g. triethylamine or pyridine) or an inorganic base.

The starting compounds of the formula VI can be prepared by one of the two processes (a) or (b) described above.

(d) When in formula I, $R_1$ represents a hydrogen atom, an alkyl or aralkyl radical and $R_2$ represents an alkanoyloxyalkyl, benzoyloxyalkyl or phenylacetyloxyalkyl radical, the alkyl and alkanoyl radicals having 1 to 4 carbon atoms, a (4-morpholino-6-proyl-1,3,5-triazin-2-yl)-aminoalkanol of the formula VIII is reacted, in equimolar proportions, with an $R_6$-carbonyl halide of the formula IX according to the equation

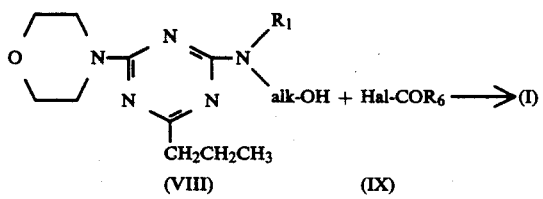

(VIII)  (IX)

In these formulae, $R_1$ has the meaning given above, alk represents a $C_1$–$C_4$ alkylene radical, $R_6$ represents a $C_1$–$C_4$ alkyl radical, phenyl or benzyl and Hal represents a halogen atom, preferably a chlorine atom This reaction is known per se and is generally carried out in an organic solvent, such as, for example, dichloromethane. dichloroethane or pyridine, at a temperature between 0° C. and 25° C. and in the presence of an acid acceptor, such as an organic tertiary base (e.g. triethylamine or pyridine) or an inorganic base.

The starting compounds of the formula VIII can be prepared by one of the two processes (a) or (b) described above.

(e) When in formula I, $R_1$ represents a hydrogen atom, an alkyl or aralkyl radical and $R_2$ represents a $CONR_4R_5$ group, in which $R_4$ and $R_5$ represent a hydrogen atom or an alkyl radical, the alkyl radicals having 1 to 4 carbon atoms, a phenyl (4-morpholino-6-propyl-1,3,5-triazin-2-yl)-carbamate of the formula X is reacted with a nitrogen compound of the formula $HNR_4R_5$ (XI) according to the equation

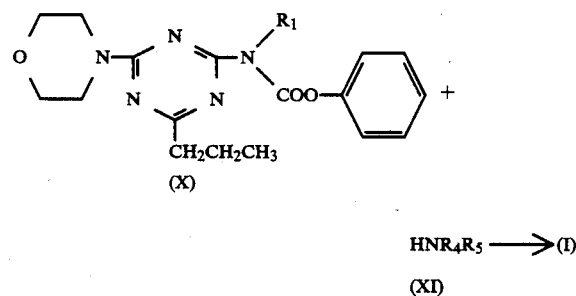

In these formulae, $R_1$, $R_4$ and $R_5$ have the meanings given above. This reaction is generally carried out in an inert solvent, such as dichloromethane, at a temperature between −45° C. and +25° C. The starting compounds of the formula X can be prepared according to process (c) above, by reacting a 2-amino-4-morpholino-6-propyl-1,3,5 -triazine of the formula VI, in which $R_1$ has the meaning given above with an $R_3$-carbonyl halide of the formula VII, in which $R_3$ represents the phenoxy radical and Hal represents a halogen atom, preferably a chlorine atom.

(f) When in formula I, $R_1$ represents a hydrogen atom, an alkyl or aralkyl radical and $R_2$ represents an aminocarbonyloxyalkyl radical, the alkyl radicals having 1 to 4 carbon atoms, ammonia is reacted with a 2-morpholino-4-(phenoxycarbonyloxyalkylamino)-6-propyl-1,3,5-triazine of the formula XII according to the equation

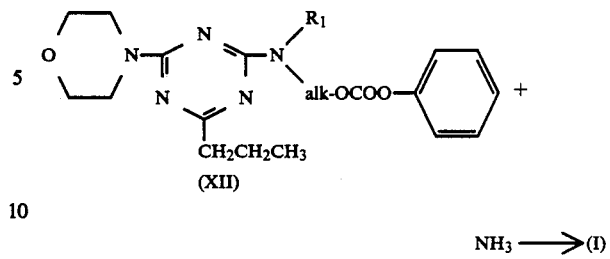

In these formulae, $R_1$ has the meaning given above and alk represents a $C_1$–$C_4$ alkylene radical. This reaction is generally carried out in an inert solvent, such as dichloromethane, at a temperature between −35° C. and −45° C. The starting compounds of the formula XII can be prepared according to process (d) above, by reacting a (4-morpholino-6-propyl-1,3,5-triazin-2-yl)aminoalkanol of the formula VIII with a phenyl haloformate of the formula XIII according to the equation

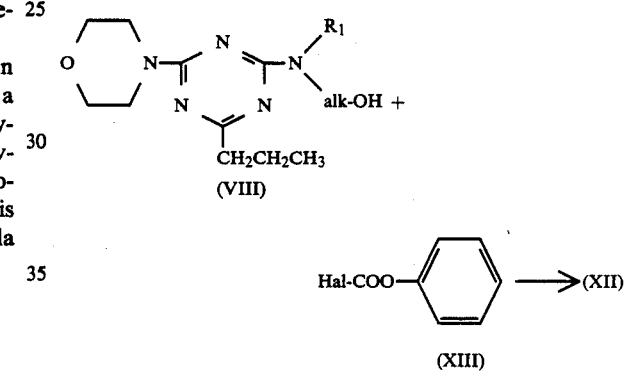

In these formulae, $R_1$ has the meaning given above, alk represents a $C_1$–$C_4$ chlorine atom.

(g) When in formula I, $R_1$ represents the acetyl radical and $R_2$ an acetoxyalkyl radical, the alkyl radical of which has 1 to 4 carbon atoms, at least two moles of an acetyl halide, preferably acetyl chloride, are reacted with one mole of a (4-morpholino-6-propyl-1,3,5-triazin-2-yl)aminoalkanol of the formula XIV according to the equation

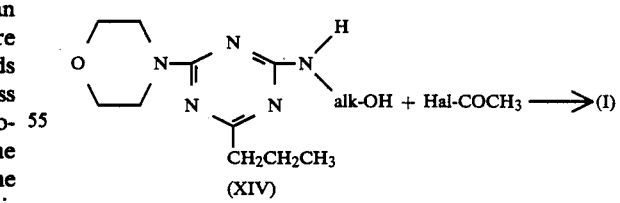

In these formulae, alk represents a $C_1$–$C_4$ alkylene radical and Hal represents a halogen atom, preferably a chlorine atom. This reaction is carried out in an inert solvent, such as dichloromethane, at a temperature between room temperature and the boiling point of the solvent and in the presence of a base, such as triethylamine. The starting compounds of the formula XIV can be prepared according to one of the two processes (a) or (b) described above.

The non-toxic pharmaceutically acceptable acid addition salts can be prepared from the 2-amino-4-morpholino-6-propyl-1,3,5-triazines of the formula I by methods which are known per se.

The following examples illustrate the present invention without limiting it.

EXAMPLE 1 PREPARATION ACCORDING TO PROCESS (A).

2-[(4morpholino-6-propyl-1,3,5-triazin-2-yl)amino]-ethanol (compound 1)

145.5 g (0.6 moles of 2-chloro-4-morpholino-6-propyl-1,3,5-triazine are dissolved in 600 ml of dioxane. A solution of 444 g (7.28 moles of 2aminoethanol in 600 ml of dioxane is introduced dropwise into this solution the course of about 80 minutes, with thorough stirring. The reaction mixture is then heated under reflux for 7 hours. It is cooled, 2-aminoethanol hydrochloride which has formed is separated off by decantation and dioxane is removed under reduced pressure. The residue obtained is dissolved in 5 liters of diethyl ether. This solution is washed with water and the washing water is extracted again with dichloromethane. The organic phases are combined and dried over magnesium sulfate. The solvent is removed under reduced pressure. The solid residue obtained is recrystallized from a 50:50 mixture (v/v) of ethyl acetate-petroleum ether. 139.8 g of 2-[(4-morpholino-6-propyl-1,3,5-triazin-2-yl)amino]-ethanol are obtained.

Yield: 88%. M.P.: 95°–99° C.

| Analysis for $C_{12}H_{21}N_5O_2$ in % | | | |
|---|---|---|---|
| calc. | C 53.91 | H 7.92 | N 26.20 |
| found | 54.30 | 8.10 | 26.13 |

The 2-[(4-morpholino-6-propyl-1,3,5-triazin-2-yl)amino]-ethanol can be in two different crystalline forms, depending on whether the product has been recrystallized from methanol (M.P.: 97°–99° C.) or from toluene (M.P.:89°–90° C.).

The compounds of the formula I summarized in Table I are prepared in the same manner.

TABLE I

2-R-4-morpholino-6-propyl-1,3,5-triazines

| Compound | R Substituent | Moles (1) | Yield (%) | M.P. (°C.) | Analysis calc. (%) | found (%) |
|---|---|---|---|---|---|---|
| 2 | NHOH | 1.1 (2) | 51.6 | 93–94 | C 55.68 | 55.70 |
|   |   |   |   |   | H 8.20 | 8.19 |
|   |   |   |   |   | N 32.24 | 32.19 |
| 3 | NHCH$_2$CH$_2$CH$_2$OH | 2 | 86.6 | 95–96 | C 55.51 | 55.02 |
|   |   |   |   |   | H 8.18 | 8.26 |
|   |   |   |   |   | N 24.91 | 24.42 |
| 4 | NH—(CH$_2$)$_3$—CH$_2$OH | 2 | 74.6 | 79–80 | C 56.95 | 56.95 |
|   |   |   |   |   | H 8.47 | 8.61 |
|   |   |   |   |   | N 23.73 | 23.42 |
| 5 | NHCH$_2$—CH(OH)—CH$_3$ | 3 | 90.0 | 104–105 | C 55.52 | 55.50 |
|   |   |   |   |   | H 8.19 | 8.00 |
|   |   |   |   |   | N 24.91 | 23.48 |
| 6 | NHCH$_2$—CH(OH)—C$_2$H$_5$ | 1 (3) | 22.0 | 56–57 | C 56.95 | 56.76 |
|   |   |   |   |   | H 8.47 | 8.37 |
|   |   |   |   |   | N 23.73 | 23.50 |
| 7 | NH—CH(C$_2$H$_5$)—CH$_2$OH | 2 | 75.4 | 90–91 | C 56.95 | 56.92 |
|   |   |   |   |   | H 8.47 | 8.40 |
|   |   |   |   |   | N 23.73 | 23.60 |
| 8 | NH—C(CH$_3$)$_2$—CH$_2$OH | 2 | 32.2 | 85–86 | C 56.95 | 57.87 |
|   |   |   |   |   | H 8.47 | 8.12 |
|   |   |   |   |   | N 23.73 | 24.24 |
| 9 | N(CH$_3$)—CH$_2$CH$_2$OH | 2 | 62.6 | 32–33 | C 55.51 | 55.48 |
|   |   |   |   |   | H 8.19 | 8.30 |
|   |   |   |   |   | N 24.91 | 24.86 |
| 10 | NHCH$_2$CH$_2$OCH$_3$ | 2 | 42.7 | 44–45 | C 55.52 | 55.60 |
|   |   |   |   |   | H 8.19 | 8.20 |
|   |   |   |   |   | N 24.91 | 24.99 |
| 11 | NHCH$_2$CHOHCH$_2$OH | 2 | 68.7 | 119–120 | C 52.52 | 52.69 |
|   |   |   |   |   | H 7.74 | 7.76 |
|   |   |   |   |   | N 23.57 | 23.60 |
| 12 | NH—C(CH$_2$OH)$_3$ | 2 | 61.0 | 110–111 | C 51.37 | 50.94 |
|   |   |   |   |   | H 7.64 | 7.53 |
|   |   |   |   |   | N 21.41 | 21.16 |
| 13 | NH—C(CH$_2$OH)$_2$—CH$_3$ | 2 | 48.0 | 121–122 | C 54.02 | 54.13 |
|   |   |   |   |   | H 8.04 | 8.00 |
|   |   |   |   |   | N 22.5 | 22.2 |
| 14 | N(CH$_2$C$_6$H$_5$)C$_2$H$_4$OH | 2 | 50 | 57–58 | C 63.86 | 64.60 |
|   |   |   |   |   | H 7.56 | 7.76 |
|   |   |   |   |   | N 19.6 | 19.8 |
| 15 | NHCH(CH$_2$OH)—CHOHC$_6$H$_5$ | 2 | 63 | 107–108 | C 61.13 | 62.00 |
|   |   |   |   |   | H 7.24 | 7.45 |
|   |   |   |   |   | N 18.77 | 18.92 |
| 16 (4) | NHCH$_2$CHOHCH$_3$ | 2 | 38 | 97–98 | C 55.52 | 56.30 |
|   |   |   |   |   | H 8.19 | 8.42 |
|   |   |   |   |   | N 24.91 | 24.70 |

TABLE I-continued
2-R-4-morpholino-6-propyl-1,3,5-triazines

| Compound | R Substituent | Moles (1) | Yield (%) | M.P. (°C.) | Analysis calc. (%) | found (%) |
|---|---|---|---|---|---|---|
| 17 (5) | NHCH$_2$CHOHCH$_3$ | 2 | 49 | 94–95 | C 55.52 | 55.64 |
|  |  |  |  |  | H 8.19 | 8.13 |
|  |  |  |  |  | N 24.91 | 24.73 |
| 18 | NHCH$_2$–(cyclohexyl)–OH | 2 | 63 | 75–76 | C 60.90 | 59.83 |
|  |  |  |  |  | H 8.66 | 8.73 |
|  |  |  |  |  | N 20.99 | 20.48 |
| 19 (6) | (pyrrolidinyl)–CH$_2$OH | 2 | 47 | 134–136 | C 52.40 | 52.48 |
|  |  |  |  |  | H 7.57 | 7.40 |
|  |  |  |  |  | N 20.38 | 19.83 |
| 20 | NHN(CH$_3$)$_2$ | 2 | 63.6 | 105–106 | C 54.14 | 54.39 |
|  |  |  |  |  | H 8.97 | 8.81 |
|  |  |  |  |  | N 31.58 | 31.65 |

(1) number of moles of amine per mole of starting compound;
(2) in the presence of 2 moles of triethylamine;
(3) in the presence of 1 mole of triethylamine;
(4) enantiomer with S configuration; $[\alpha]_D^{25}$ = +15.3 (C = 1, methanol);
(5) enantiomer with R configuration; $[\alpha]_D^{25}$ = −16.1 (C = 1, methanol);
(6) hydrochloride.

The 2-chloro-4-morpholino-6-propyl-1,3,5-triazine used as starting compound for the synthesis of the compounds mentioned in this example has been prepared according to the method described by T. TSUJIKAWA et al., (Yakugaku Zasshi,95,(1975),5-12-520) starting from 2,4-dichloro-6-propyl-1,3,5-triazine. This last compound has been prepared according to the process of R. HIRT et al. (Helv.Chim.Acta,33,(1950),1365–69).

EXAMPLE 2 PREPARATION ACCORDING TO PROCESS (B)

(a) Obtaining the starting 2-[(4-chloro-6-propyl-1,3,5-triazin-2-yl)amino]-ethanol.

24.4 g (0.4 mole) of 2-aminoethanol, dissolved in 100 ml of dioxane, are added dropwise into a solution of 38.4 g (0.2 mole) of 2,4-dichloro-6-propyl-1,3,5-triazine in 100 ml of dioxane at room temperature. After the addition, stirring is continued overnight. The 2-aminoethanol hydrochloride is filtered off and the filtrate is evaporated under reduced pressure. The residue obtained is recrystallized from a mixture of ethyl acetate-hexane 50:50 (v/v). 41.5 g of 2-[(4-chloro-6-propyl-1,3,5-triazin-2-yl)amino]-ethanol are obtained.

Yield: 96%. M.P.: 87°–88° C.

| Analysis for C$_8$H$_{13}$ClN$_4$O in % | | | | |
|---|---|---|---|---|
|  | C | H | N | Cl |
| calc. | 44.34 | 6.00 | 25.88 | 16.40 |
| found | 44.42 | 6.17 | 25.69 | 16.5 |

(b) Preparation of 2-[(4-morpholino-6-propyl-1,3,5-triazin-2-yl)amino]-ethanol.

Variant 1

10.83 g (0.05 mole) of 2-[(4-chloro-6-propyl-1,3,5-triazin-2-yl)amino]-ethanol and 8.7 g (0.10 mole) of morpholine are mixed in 150 ml of dioxane. The temperature of the mixture rises spontaneously to 41° C. It is then heated under reflux for 30 minutes and cooled and the morpholine hydrochloride which has formed is filtered off. The filtrate is evaporated and the residue is recrystallized from a 50:50 mixture (v/v) of ethyl acetate-hexane. 11.8 g of 2-[(4-morpholino-6-propyl-1,3,5-triazin-2-yl)amino]-ethanol are obtained.

Yield: 88.4%. M.P.: 93°–94° C. The product, recrystallized from methanol, has a melting point of 97°–98° C. and is identical to compound 1 prepared in example 1.

Variant 2

10.83 g (0.05 mole) of 2-[(4-chloro-6-propyl-1,3,5-triazin-2-yl)amino]-ethanol and 15.15 g (0.15 mole) of N-methylmorpholine are mixed in 100 ml of dioxane. The mixture is heated under reflux for 20 hours; it is then cooled and the dioxane is removed under reduced pressure. The residue is dissolved in 200 ml of ethyl acetate. The solution is washed twice with 50 ml of water, dried over sodium sulfate and concentrated. The product crystallizes during the evaporation. 9.23 g of 2-[(4-morpholino-6-propyl-1,3,5-triazin-2-yl)amino]-ethanol identical to the product obtained above are obtained.

EXAMPLE 3. PREPARATION ACCORDING TO PROCESS (C)

(a) Obtaining the starting 2-amino-4-morpholino-6-propyl-1,3,5-trizines.

1. 2-Amino-4-morpholino-6-propyl-1,3,5-triazine (hydrochloride).

This product is described by S. MURAI et al. in Japanese patent application No. 69,688/74 (Chem.Abstr.81,(1974),136188x). It can be prepared in the following manner.

87 g (1 mole) of morpholine and 8.6 g (0.05 mole) of 2-amino-4-chloro-6-propyl-1,3,5-triazine are mixed. The temperatures of the mixture rises spontaneously to 54° C. The mixture is then heated under reflux for 5 hours.

The reaction mixture is evaporated under reduced pressure and the residue obtained is redissolved in ethyl acetate. The solution is washed three times with water and then dried over sodium sulfate. The solvent is removed under reduced pressure and the residue is recrystallized from hexane. 9.1 g of 2-amino-4-morpholino-6-propyl-1,3,5-triazine are obtained.

Yield: 82%. M.P.: 127°–128° C.

Hydrochloride: M.P.: 210°–211° C. (isopropyl alcohol-ether).

| Analysis for $C_{10}H_{17}N_5O \cdot HCl$ in % | | | | |
|---|---|---|---|---|
| calc. | C 46.24 | H 6.94 | N 26.97 | $Cl^-$ 13.68 |
| found | 46.21 | 6.90 | 26.78 | 13.61 |

The 2-amino-4-chloro-6-propyl-1,3,5-triazine used as the starting compound in this reaction has been prepared according to the method of S. MURAI et al. Japanese patent application No. 69,688/74).

2. 2-(Methylamino)-4-morpholino-6-propyl-1,3,5-triazine (hydrochloride). A solution containing 8.7 g (0.1 mole) of morpholine in 50 ml of dioxane is added to a solution containing 5.6 g of (0.03 mole) of 2-chloro-4-(methylamino)-6-propyl-1,3,5-triazine in 50 ml of dioxane. The mixture is heated under reflux for 5 hours. It is then cooled and the morpholine hydrochloride which has formed is filtered off. The solvent is removed under reduced pressure and the residue is taken up in chloroform. The mixture is washed with water and the organic phase is dried over sodium sulfate. The solvent is evaporated and the residue is recrystallized from ethyl acetate. 5.3 g of 2-(methylamino)-4-morpholino-6-propyl-1,3,5-triazine are obtained.

Yield: 74%. M.P.: 131°–133° C.

The product obtained is dissolved in hot isopropyl alcohol. The equivalent amount of hydrochloric acid, dissolved in ethyl ether, is added to this solution. The hydrochloride crystallizes upon cooling. The crystals are filtered off, washed with diethyl ether and dried.

Yield: 75%. M.P.: 177°–178° C.

| Analysis for $C_{11}H_{19}N_5O \cdot HCl$ in % | | | | |
|---|---|---|---|---|
| calc. | C 48.26 | H 7.31 | N 25.59 | $Cl^-$ 12.97 |
| found | 48.38 | 7.40 | 25.57 | 12.64 |

The 2-chloro-4-(methylamino)-6-propyl-1,3,5-triazine used as the starting compound in this reaction has been prepared according to the method of T. TSUJIKAWA et al., (Yakugaku Zasshi,95,(1975),5-12–520).

(b) Preparation of the 2-amino-4-morpholino-6-propyl-1,3,5-triazines.

1. N-(4-Morpholino-6-propyl-1,3,5-triazin-2-yl)-acetamide (compound 21). 4 g (0.05 mole) of acetyl chloride are added dropwise into a solution of 11.2 g (0.05 mole) of 2-amino-4-morpholino-6-propyl-1,3,5-triazine in 100 ml of anhydrous pyridine at room temperature. The mixture is stirred for 6 hours and then allowed to stand for 48 hours. The pyridine hydrochloride is filtered off and the filtrate is evaporated under reduced pressure. The residue obtained is taken up once in toluene, and the mixture is evaporated again. The residue is then taken up in dichloromethane and the solution is washed with water and dried over sodium sulfate. The residue obtained after evaporation of the solvent is purified by chromatography over silica (eluent: 90:10 (v/v) dichloromethane-ethanol) and the product is finally recrystallized from ethyl acetate. 5.75 g of N-(4-morpholino-6-propyl-1,3,5-triazin-2-yl)-acetamide are obtained.

Yield 43.4% M.P.: 141°–142° C. (Compound 21a).

Hydrochloride: M.P.: 145°–146° C. (isopropyl alcohol-ether).

(Compound 21b)

| Analysis for $C_{12}H_{19}N_5O_2 \cdot HCl$ in % | | | | |
|---|---|---|---|---|
| calc. | C 47.76 | H 6.63 | N 23.22 | $Cl^-$ 11.77 |
| found | 47.78 | 6.73 | 2.80 | 11.62 |

2. N-(4-Morpholino-6-propyl-1,3,5-triazin-2-yl)-benzamide (hydrochloride) (compound 22).

A solution of 7.7 g (0.055 mole) of benzoyl chloride in 50 ml of dichloroethane and a solution of 5.5 g (0.055 mole) of triethylamine in ml of dichloroethane are successively added into a solution of 11.2 g (0.05 mole) of 2-amino-4-morpholino-6-propyl-1,3,5-triazine in 200 ml of dichloroethane at room temperature. The mixture is heated under reflux for 6 hours and cooled to room temperature. It is washed successively with water, with an aqueous solution of sodium bicarbonate and then with water once again. The organic phase is dried over sodium sulfate and the solvent is evaporated under reduced pressure. The residue obtained is chromatographed on silica (eluent: 95:5 (v/v) dichloromethane-ethanol) and finally recrystallized from a 50:50 mixture (v/v) of diethyl etherhexane. The product forms a hydrochloride in the diethyl ether. 12.1 g of N-(4-morpholino-6-propyl-1,3,5-triazin-2-yl)-benzamide hydrochloride are thus obtained.

| Analysis for $C_{17}H_{21}N_5O_2 \cdot HCl$ in % | | | | |
|---|---|---|---|---|
| calc. | C 56.12 | H 6.05 | N 19.26 | $Cl^-$ 9.77 |
| found | 56.30 | 6.50 | 19.16 | 9.54 |

The compounds summarized in Table II are prepared, as indicated, either the method of example 3(b)1. or by the method of example 3(b)2. above.

TABLE II

| 2-R-4-Morpholino-6-propyl-1,3,5-triazines. | | | | | | |
|---|---|---|---|---|---|---|
| | | | | | Analysis | |
| Compound | R Substituent | Method | Yield (%) | M.P. (°C.) | calc. (%) | found (%) |
| 23 | $NHCOCH_2C_6H_5$ | 3b.1 | 51.3 | 110–113 | C 63.34 | 63.18 |
| | | | | | H 6.74 | 6.85 |
| | | | | | N 20.52 | 20.55 |
| 24 | $NHCOCH(CH_3)_2$ | 3b.1 | 34.3 | 141 | C 57.34 | 56.84 |
| | | | | | H 7.85 | 7.84 |
| | | | | | N 23.89 | 23.70 |
| 25a | $N(CH_3)COCH_3$ | 3b.1 | 34.8 | 60–61 | C 55.91 | 56.02 |
| | | | | | H 7.53 | 7.57 |
| | | | | | N 25.09 | 25.05 |
| 25b (1) | $N(CH_3)COCH_3$ | 3b.1 | 75.5 | 104–105 | C 49.44 | 48.78 |
| | | | | | H 6.97 | 7.01 |
| | | | | | N 22.19 | 22.43 |

TABLE II-continued

2-R-4-Morpholino-6-propyl-1,3,5-triazines.

| Compound | R Substituent | Method | Yield (%) | M.P. (°C.) | Analysis calc. (%) | found (%) |
|---|---|---|---|---|---|---|
| 26 | N(CH$_3$)COCH(CH$_3$)$_2$ | 3b.1 | 38.5 | 36–37 | C 58.62 | 58.78 |
|  |  |  |  |  | H 8.16 | 8.33 |
|  |  |  |  |  | N 22.80 | 22.62 |
| 27 (1) | N(CH$_3$)COC$_6$H$_5$ | 3b.2 | 46.5 | 122 | C 57.22 | 56.78 |
|  |  |  |  |  | H 6.36 | 6.40 |
|  |  |  |  |  | N 18.54 | 18.28 |
| 28 | NH—COOC$_6$H$_5$ | 3b.2 | 24.8 | 154–155 | C 59.48 | 59.60 |
|  |  |  |  |  | H 6.12 | 6.32 |
|  |  |  |  |  | N 20.41 | 20.31 |
| 29 (1) | NH-CO-C$_6$H$_4$-pCl | 3b.2 | 66 | 205–206 | C 51.27 | 51.19 |
|  |  |  |  |  | H 5.31 | 5.34 |
|  |  |  |  |  | N 17.58 | 17.49 |
| 30 | N(CH$_3$)COC$_6$H$_4$-pCl | 3b.2 | 72 | 96–97 | C 57.52 | 58.07 |
|  |  |  |  |  | H 5.90 | 6.17 |
|  |  |  |  |  | N 18.63 | 18.65 |
| 31 (1) | NHCOC$_6$H$_4$-pOCH$_3$ | 3b.2 | 33 | 199 | C 54.89 | 54.83 |
|  |  |  |  |  | H 6.14 | 6.17 |
|  |  |  |  |  | N 17.78 | 17.80 |
| 32 (1) | N(CH$_3$)COC$_6$H$_4$-pOCH$_3$ | 3b.2 | 56 | 120 | C 55.94 | 53.40 |
|  |  |  |  |  | H 6.42 | 6.48 |
|  |  |  |  |  | N 17.17 | 17.22 |
| 33 (1) | NHCOC$_6$H$_4$-pCH$_3$ | 3b.2 | 53 | 188 | C 57.21 | 57.45 |
|  |  |  |  |  | H 6.40 | 6.42 |
|  |  |  |  |  | N 18.53 | 18.73 |
| 34 (1) | N(CH$_3$)COC$_6$H$_4$-pCH$_3$ | 3b.2 | 74 | 99 | C 58.23 | 58.08 |
|  |  |  |  |  | H 6.69 | 6.73 |
|  |  |  |  |  | N 17.87 | 18.11 |
| 35 | N(CH$_3$)COC$_6$H$_3$-3,4-ki-OCH$_3$) | 3b.2 | 70 | 73 | C 59.84 | 60.12 |
|  |  |  |  |  | H 6.78 | 7.09 |
|  |  |  |  |  | N 17.44 | 17.45 |
| 36 | NHCOC$_6$H$_3$-(3,4-di-CH$_3$) | 3b.1 | 45 | 232 | C 58.23 | 58.42 |
|  |  |  |  |  | H 6.69 | 6.65 |
|  |  |  |  |  | N 17.87 | 17.72 |

(1) hydrocholoride

EXAMPLE 4. PREPARATION ACCORDING TO PROCESS (D)

1. 2-[[2-Acetoxy)ethyl]amino]-4-morpholino-6-propyl-1,3,5-triazine (compound 37).

4 3 g (0.055 mole) of acetyl chloride, dissolved in 50 ml of dichloromethane, and 5.5 g (0.055 mole) of triethylamine, dissolved in 50 ml of dichloromethane, are simultaneously introduced, between 0° and 5° C., into a solution of 13.4 g (0.05 mole) of 2-[(4-morpholino-6-propyl-1,3,5-triazin-2-yl)amino]-ethanol (compound 1 prepared in Example 1) in 200 ml of dichloromethane. The addition of these two reagents is regulated in a manner such that the acid chloride is always present in the reaction mixture in excess with respect to the triethylamine. The mixture is stirred for one hour at 5° C. and then for 12 hours at room temperature. The reaction mixture is washed successively with an aqueous solution of sodium bicarbonate and with water. It is dried over sodium sulfate and the solvent is evaporated under reduced pressure. The residue crystallizes in a mixture of toluene-hexane 1:2. The product obtained is first purified by chromatography on silica (eluent: 95:5 (v/v) dichloromethane-ethanol) and is then firstly recrystallized from a mixture of toluene-hexane 1:1. 9.3 g of 2-[[2-(acetoxy)ethyl]amino]-4-morpholino-6-propyl-1,3,5-triazine are obtained.

Yield: 60%. M.P.: 94°–95° C.

| Analysis for C$_{14}$H$_{23}$N$_5$O$_3$ in % | | | |
|---|---|---|---|
| calc. | C 54.37 | H 7.44 | N 22.65 |
| found | 54.98 | 7.69 | 22.62 |

The compounds summarized in Table III are prepared in the same manner.

TABLE III

2-R-4-Morpholino-6-propyl-1,3,5-triazines.

| Compound | R Substituent | Yield(%) | M.P.(°C.) | Analysis calc. (%) | found (%) |
|---|---|---|---|---|---|
| 38 | NH(CH$_2$)$_2$O-COCH(CH$_3$)$_2$ | 59.3 | 54–55 | C 56.97 | 56.86 |
|  |  |  |  | H 8.01 | 8.04 |
|  |  |  |  | N 20.77 | 20.74 |
| 39 | NH(CH$_2$)$_2$O—COC$_6$H$_5$ | 67.4 | 98–99 | C 61.46 | 61.52 |
|  |  |  |  | H 6.74 | 6.75 |
|  |  |  |  | N 18.87 | 18.91 |
| 40 | NH(CH$_2$)$_2$O—COCH$_2$C$_6$H$_5$ | 63.4 | 63–64 | C 62.34 | 62.45 |
|  |  |  |  | H 7.01 | 7.07 |
|  |  |  |  | N 18.18 | 18.15 |

EXAMPLE 5. PREPARATION ACCORDING TO PROCESS (E)

N,N-Dimethyl-N'-(4-morpholino-6-propyl-1,3,5-triazin-2-yl)-urea (compound 41).

A gaseous stream of dimethylamine is passed through a solution of 5 g (0.0145 mole) of phenyl (4-morpholino-6-propyl-1,3,5-triazin-2-yl)carbamate (compound 28 prepared in example 3) in 100 ml of anhydrous dichloromethane for three hours at a temperature of 20° C. The mixture is then allowed to stand for 12 hours. It is washed successively with a dilute sodium hydroxide solution and with water. The organic phase is dried over sodium sulfate and the solvent is evaporated under reduced pressure. The residue obtained crystallizes in a 50:50mixture (v/v) of ethyl acetate-hexane. 1.7 g of N,N-dimethyl-N'-(4-morpholino-6-propyl-1,3,5-triazin-2-yl)-urea is obtained.

Yield: 39.9%. M.P.: 110°–111° C.

| Analysis for $C_{13}H_{22}N_6O_2$ in % | | | |
|---|---|---|---|
| calc. | C 53.06 | H 7.48 | N 28.57 |
| found | 53.20 | 7.69 | 28.67 |

EXAMPLE 6. PREPARATION ACCORDING TO PROCESS (F)

2-[[2-[(Aminocarbonyl)oxy]ethyl]amino]-4-morpholino-6-propyl-1,3,5-triazine (compound 42).

19.4 g (0.05 mole) of 2-morpholino-4-[[2-[(phenoxycarbonyl)oxy]ethyl]amino]-6-propyl-1,3,5-triazine, dissolved in 100 ml of anhydrous dichloromethane are introduced into one liter of liquid ammonia. Stirring is continued for 7 hours at a temperature of between −35° C. and −45° C. The ammonia is then evaporated and the organic phase is washed successively with an aqueous solution of sodium bicarbonate and with water. It is dried over sodium sulfate and the solvent is evaporated under reduced pressure. The residue obtained crystallizes in a 50:50 mixture (v/v) of ethyl acetate-hexane. 15.1 g of 2-[[2-[(aminocarbonyl)oxy]ethyl]amino]-4-morpholino-6-propyl-1,3,5-triazine are obtained.

Yield: 97.4%. M.P.: 139°–140° C.

| Analysis for $C_{13}H_{22}N_6O_3$ in % | | |
|---|---|---|
| calc. | C 50.32 | H 7.09 |
| found | 50.39 | 7.15 |

The 2-morpholino-4-[[2-[(phenoxycarbonyl)oxy]ethyl]amino]-6-propyl-1,3,5-triazine used as the starting material in this example has been prepared according to the process of example 4 starting from 2-[(4-morpholino-6-propyl-1,3,5-triazin-2-yl)amino]-ethanol and phenyl chloroformate.

Yield: 85%. M.P.: 83°–84° C.

| Analysis for $C_{19}H_{25}N_5O_4$ in % | | | |
|---|---|---|---|
| calc. | C 58.91 | H 6.46 | N 18.0 |
| found | 58.99 | 6.60 | 18.1 |

EXAMPLE 7. PREPARATION ACCORDING TO PROCESS (G)

N-[2-(Acetoxy)ethyl]-N-(4-morpholino-6-propyl-1,3,5-triazin-2-yl)-acetamide (compound 43).

A solution of 11.8 g (0.15 mole) of acetyl chloride in 50 ml of dichloroethane and a solution of 15 g (0.15 mole) of triethylamine in 50 ml of dichloroethane are added to a suspension of 13.4 g (0.05 mole) of 2-[(4-morpholino-6-propyl-1,3,5-triazin-2-yl)amino]-ethanol (compound 1 prepared in example 1) in 250 ml of dichloroethane kept at a temperature of about 20° C. This addition is carried out in the following manner: half of the acid chloride is first added and the mixture is allowed to react for 15 minutes, and half of the triethylamine is then added: the remainder of the acid chloride is then introduced, the mixture is allowed to react for a further 15 minutes and is heated to 55° C. and finally the remainder of the triethylamine is introduced. The mixture obtained is heated under reflux for 7 hours. It is then allowed to stand overnight at room temperature. It is washed successively with an aqueous solution of sodium bicarbonate and with water. It is dried over sodium sulfate and filtered in the presence of Norit. After evaporation of the solvent under reduced pressure, the residue obtained is purified by chromatography on silica (eluent: 95:5 (v/v) dichloromethane-ethanol). The product obtained crystallizes in hexane in the cold. 6.35 g of N-[2-(acetoxy)ethyl]-N-(4-morpholino-6-propyl-1,3,5-triazin-2-yl)-acetamide are obtained.

Yield: 36.2%. M.P.: 49°–50° C.

| Analysis for $C_{16}H_{25}N_5O_4$ in % | | | |
|---|---|---|---|
| calc. | C 54.70 | H 7.12 | N 19.94 |
| found | 55.22 | 7.22 | 20.0 |

As indicated above, the 2-amino-4-morpholino-6-propyl-1,3,5-triazines of the formula I and their non-toxic pharmaceutically acceptable acid addition salts have the property of correcting the effects of hypofunctioning of the cholinergic system. This advantageous property is demonstrated by a series of pharmacological studies whereby it is shown that the compounds according to the invention have certain effects similar to those of well-known cholinergic compounds, such as oxotremorine, arecoline or physostigmine, or else counteract the effect of a cholinergic antagonist such as scopolamine. The compounds of the present invention were subjected to pharmacological tests, the results of which are reproduced below.

1. Potentiation of the cholinergic effects of oxotremorine. The purpose of this test (R. C. RATHBUN et al., Psychopharmacologia,4,(1963),114–125) is to demonstrate that the compounds according to the invention potentiate the central and peripheral cholinergic effects caused by the administration of a low dose of oxotremorine to mice. The degree of peripheral cholinergic activation is measured by the salivatory effect quantified by the following rating system:

score 0: the saliva does not exceed that secreted by a normal mouse:

score 1: a little saliva is found around the teeth:

score 2: the saliva forms a narrower band around the mouth;

score 4: the saliva wets a surface underneath the chin;

score 6: the saliva runs from the mouth, for example onto the forelegs.

The intermediate scores are not used, and the saliva is wiped away after each observation.

The degree of central cholinergic activation is measured by the tremogenic effect quantified by the following rating system:

score 0: no tremor;

score 1: slight and periodic occasional tremors;

score 2: moderate and slight tremors often repeated;

score 4: accentuated tremors, but interrupted by periods of calm:

score 6: very accentuated and almost continuous tremors.

Male NMRI mice (20 to 25 g) are divided into four groups of five animals, that is to say: one control group and three treated groups. The compound to be tested is administered intraperitoneally (to the three treated groups) 20 minutes before the administration of the oxotremorine, at a dose which differs for each of the treated groups. The oxotremorine is administered intraperitoneally to the treated groups and to the control group at a dose of 0.05 mg/kg dissolved in 10 ml/kg of physiological salt solution. This dose approximately corresponds to the minimum dose of oxotremorine which causes tremors and salivation After the administration of the oxotremorine, the animals are placed individually in small cages and are observed at regular intervals of 5 minutes until the cholinergic effects have disappeared completely. For each of the groups, the individual scores recorded at each observation period are summed; this enables to plot a curve showing the sum of the scores as a function of time, which is characteristic for each group.

The mean values of the areas under the curves obtained for each of the treated groups are compared with the mean value of the area under the curve corresponding to the control group and is subjected to statistical analysis by the Mann-Whitney method. From this comparison, a "minimum active dose" can be determined. This "minimum active dose" is the minimum dose of compound needed for a potentiation of the salivatory or tremogenic effect of the oxotremorine still to be observed, or in other words for an area greater than the area under the curve obtained for the control group to be obtained.

The results obtained in this test demonstrate that the compounds according to the invention potentiate the salivatory effect of oxotremorine at a minimum dose of from 7.7 to 107 mg/kg and potentiate the tremogenic effect at a minimum dose of from 8 to 112 mg/kg. Moreover, the minimum active doses do not have cholinergic effects of their own and are far remote from the lethal doses determined in the Irwin's test. In addition, this test demonstrates that certain compounds according to the invention, when administered at the minimum active dose, have effects which last longer than methyl 1,2,5,6-tetrahydro-1-methyl-3-pyridinecarboxylate (arecoline), a well-known cholinergic compound. The compounds of the invention thus show potentiation of the salivatory and tremogenic effects of oxotremorine 20 minutes after being administered at the minimum active dose, whereas under the same conditions, arecoline gives no potentiation.

2. Inhibition of hyperactivity induced by scopolamine. An animal placed for the first time in a new environment manifests intense exploratory activity in this new medium. The progressive reduction and then the disappearance of this exploratory activity, in other words habituation to the new medium, can be considered as an elementary form of learning. This elementary form of learning is sensitive to the influence of drugs which facilitate or adversely affect learning (A. PLATEL et al., Psychopharmacology, 78,(1982),346–352). Thus, for example, scopolamine, a compound which causes mnemic disorders, induces exploratory hyperactivity in rats placed in a new environment; this phenomenon is associated with the central anticholinergic activity of this compound (W.J. STEWART et al., Psychopharmacologia,44,(1975),291-295). In contrast, a cholinergic agonist such as physostigimine counteracts the hyperactivity induced by scopolamine. In the test described below, the compounds of the invention are administered either in physiological salt solution or in a suitable vehicle (generally a citrate buffer of pH 5), depending on their solubility.

This test reveals for the compounds according to the invention an activity comparable to that of physostigmine.

It is based on the original technique described by A. PLATEL (loc.cit.) on the one hand and on the process for automation of the recording of measurements described by H. J. TAUGER et al. (J.Neuroscience Methods,10,(1984),237–245) on the other hand. In this test, male Sprague-Dawley SPF (Specific Pathogen Free; 160 to 200 g) rats are used. During the week preceding the experiment, these animals are housed under normal conditions in groups of 15 animals in standard grid cages, and food and drink are freely accessible. At the start of the experiment, the rats are divided into 4 homogeneous groups of 10 animals and are acclimatized to the site of the experiment for one hour. Each group of animals is then subjected to a predetermined treatment:

group 1 receives two simultaneous intraperitoneal injections of physiological salt solution or of the vehicle used;

group 2 receives one intraperitoneal injection of physiological salt solution or of the vehicle used and one intraperitoneal injection of 0.5 mg/kg of scopolamine in solution;

group 3 receives one intraperitoneal injection of the compound to be tested in solution in a suitable vehicle and one intraperitoneal injection of physiological salt solution or of the vehicle used;

group 4 receives one intraperitoneal injection of the compound to be tested and one intraperitoneal injection of 0.5 mg/kg of scopolamine.

Thirty minutes after this treatment, the four groups of animals are tested simultaneously. To this end, each group is distributed in a square chamber (100×100 cm) made of a grid floor and a vertical wall 50 cm in height. Each of these chambers contains 16 zones comprising 4 zones in the corners, 4 central zones and 8 peripheral zones. In addition, each chamber is fitted with 2 rows of infra-red cells arranged 2 cm above the floor for recording the horizontal movements of the animals and 2 other rows of infra-red cells arranged at a height of 10 cm above the floor for recording the vertical movements. These infra-red cells are connected to a microprocessor which allows determination of the average distances covered (in cm) by a group of animals and also determination of the average number of straightenings, as well as of the distribution of the horizontal movements in the various central and peripheral zones and in the corners, expressed as the average time stayed in these various zones. Each compound tested is studied at least at three different doses, from which the minimum active dose which inhibits the hyperactivity indu intraperitoneal administration of 0.5 mg/kg of scopolamine is determinec. The values obtained in group 2 treated only with scopolamine are then compared with those obtained in group 4 treated with both scopolamine and the compound to be tested, and the values obtained in group 4 are compared with those obtained in group 3 treated only with the compound to be tested. The control group 1 serves as a control of the action of the scopolamine administered to group 2. The differences found are evaluated statistically in all cases by the Msnn-Whitney method. The results obtained in this test have shown that the compounds of the invention have a good inhibitory activity on the hyperactivity induced by scopolamine. The minimum active doses determined for these compounds are between 1 and 89 mg/kg. However, in contrast to physostigmine, which is inactive when administered more than 15 minutes before the measurements are made, the compounds according to the invention still have an inhibitory activity when they are administered 30 minutes before the measurements are made. Their activity thus lasts longer than that of physostigmine.

3. Inhibition of the effects of scopolamine on the electroencephalogram. (EEG).

The administration of scopolamine to humans or animals induces mnemic disorders comparable to those which appear in the course of normal or pathological ageing. In patients suffering from senile dementia, Alzheimer's type, an improvement in mnesic disorders has been achieved by administration of physostigmine, a compound which inhibits acetylcholinesterase. Scopolamine administered intraperitoneally to rats at a dose of 0.5 mg/kg induces variations in the EEG spectrum, which manifest themselves by an increase in the intensity in the band at 8 Hz, a reduction in the intensity of the bands from 20.8 to 40 Hz and an increase in the overall intensity of the EEG spectrum. Physostigmine counteracts these variations. The aim of this test is to demonstrate, by means of the quantitative analytical method of the electroencephalogram, that the compounds of the invention have the property of neutralizing the effects which scopolamine exerts on the EEG spectrum (P. ETEVENON, L'Electroencephalographie sur ordinateur. Analyse quantitative et statistique. Copedith, Paris, 1978). Male albino Sprague-Dawley SPF rats (160 to 200 g) are used in this test. When the animals are 3 months old, 5 cortical electrodes are implanted permanently, aseptically and under a general anesthesia: one inert electrode, one left and one right frontal electrode, and one left and one right occipital electrode (P. ETEVENON, loc.cit.). The test is carried out when the animals are about 15 months old. In the meantime, the animals are kept in individual cages. They are given water and food ad libitum and are subjected to a regular daily cycle comprising a period of darkness between 6 o'clock in the evening and 6 o'clock in the morning. At the same time, the animals are progressively acclimatized to the cages of the sound-proof cabin which they will subsequently occupy for recording of the electroencephalograms, as well as to the experimental conditions, by intraperitoneal administration of placebo. The products are administered immediately before the EEG is recorded. The rats are divided into groups of 8 animals and 16 samples of the EEG spectra are recorded over 5 seconds (two EEG spectra per animal). The spectra obtained are then analyzed by computer (rapid Fourier transform), which enables the average of the 16 measurements performed to be determined for each group and the overall intensity of the EEG spectrum and the distribution of this intensity (in %) in the various frequency bands to be deduced for each animal. This operation (recording of the spectra) is repeated 9 times (total duration: 121 minutes).

The effect of the compound studied is deduced from the statistical comparison of the results obtained for the various groups of animals to which the compound to be tested, the scopolamine and a placebo respectively have been administered.

Table IV below shows for some of the compounds of the invention administered intraperitoneally at the dose shown in mg/kg, the percentage of reduction in the increase in the intensity of the band from 6.4 to 9.6 Hz (average 8 Hz), an increase caused by intraperitoneal administration of 0.5 mg/kg of scopolamine.

TABLE IV

Inhibition of the effects of scopolamine on the band from 6.4 to 9.6 Hz in the EEG.

| Compound | Dose (mg/kg) | Inhibition (in %) |
| --- | --- | --- |
| 1 | 5.3 | 52 |
| 7 | 29.5 | 50 |
| 9 | 8.8 | 53.3 |
| 20 | 2.7 | 66.7 |
| 21a | 2.7 | 100 |
| 22 | 3.6 | 66.7 |
| 25a | 0.88 | 46.7 |
| 26 | 3.1 | 55.6 |
| 27 | 12 | 93.8 |
| 37 | 9.9 | 53.3 |
| 43 | 11.2 | 77.8 |
| physostigmine | 0.4 | 76.8 |

The results show that the compounds of the invention, like physostigmine, inhibit the effects which scopolamine exerts on the electroencephalogram. It can be seen that this inhibition reaches and exceeds even 50% at relatively low doses far remote from the toxic doses, which is not the case for physostigmine.

4. Multiple-trial passive avoidance. The compounds of the present invention have been studied with the aim of demonstrating on the one hand their property of promoting learning expressed as the reduction in the number of trials needed to achieve a predetermined criterion, and on the other hand their property of counteracting the amnesia caused by administration of scopolamine. To this end, the method of multiple-trial passive avoidance has been used. This method is well-known for evaluating the effects which a product exerts on the memory and learning (A. FINE et al., Proc.Natl.Acad.Sci.USA,82,(1985),5227-5230).

The test is carried out on male Sprague-Dawley rats (160–200 g), which are kept in standard cages throughout the experiment. The apparatus used is a transparent square cage with 35 cm sides and 25 cm high. fitted with a grid floor which can be electrified. An insulating rubber mat ($10 \times 17$ cm) is placed on the floor in one of the corners of the cage.

To evaluate whether a compound can promote learning, the following test is carried out.

Each animal is placed on the rubber mat and the time the animal takes to decide to leave this position to explore the cage is recorded. After 20 seconds of exploration, the animal receives an electric shock (3 seconds duration) in the paws, causing a flight reaction. The rat is immediately removed from the apparatus and replaced in its original cage. This experiment is repeated until the animal remains on the rubber mat for at least 180 seconds in order to avoid the electric shock. The learning is expressed by the average number of trials needed to reach a period of 180 seconds remaining on the mat. A period of remaining on the rubber mat of 180 seconds is regarded as being the maximum performance which can be realized by the animal to avoid the electric shock. Rats which remain on the mat for this period have acquired the avoidance reflex and are replaced in their original cage without receiving the electric shock.

To evaluate whether a compound is capable of promoting mnemic retention in the course of time, the following experiment is carried out. Each animal is subjected to four tests at times 0, 4, 24 and 28 hours. In the first test (time 0), the animal is placed on the rubber pound studied (at the dose shown in the second column), are to be found.

The favorable influence of a compound in counteracting amnesia induced by scopolamine is demonstrated by the increase in the period of remaining on the mat at each observation. The differences observed are analyzed statistically by the Mann-Whitney method.

TABLE V

| | | Learning average number of trials | | Mnemic retention Period of remaining on the mat (in seconds) | | | | | | | |
| --- | --- | --- | --- | --- | --- | --- | --- | --- | --- | --- | --- |
| | Dose | | | group 3 | | | | group 4 | | | |
| Compound | (mg/kg) | group 1 | group 2 | 0 | 4 | 24 | 28 | 0 | 4 | 24 | 28 |
| 1 | 5.35 | 2.27 | 1.53 | 1.27 | 13.3 | 24.2 | 26.3 | 2.7 | 44.8 | 61.3 | 102.7 |
| 7 | 29.54 | 2.67 | 2.57 | 1.0 | 1.5 | 3.3 | 4.0 | 1.3 | 7.3 | 22.5 | 52.1 |
| 9 | 8.72 | 2.27 | 2.0 | 1.4 | 2.3 | 3.3 | 5.7 | 3.3 | 67.9 | 62.7 | 160.3 |
| 10 | 28.14 | 2.87 | 2.07 | 1.8 | 4.5 | 2.3 | 4.5 | 5.5 | 15.7 | 31.1 | 34.1 |
| 20 | 2.66 | 1.93 | 1.53 | 1.1 | 2.5 | 4.6 | 5.5 | 2.7 | 55.3 | 57.7 | 87.9 |
| 21a | 2.65 | 1.60 | 1.53 | 2.4 | 9.7 | 9.1 | 33.9 | 3.4 | 60.4 | 74.6 | 102.4 |
| 22 | 3.64 | 2.20 | 1.0 | 1.7 | 11.1 | 20.3 | 12.8 | 2.8 | 70.9 | 82.8 | 137.6 |
| 25a | 0.89 | 2.07 | 2.07 | 2.1 | 3.0 | 7.7 | 3.3 | 1.7 | 8.1 | 34.7 | 44.5 |
| 27 | 3.78 | 2.20 | 1.13 | 1.9 | 8.9 | 31.6 | 54.1 | 11.3 | 88.6 | 111.5 | 133.5 |
| 37 | 9.6 | 2.0 | 1.3 | 1.0 | 2.5 | 4.5 | 5.8 | 2.9 | 24.0 | 44.4 | 49.9 |
| 41 | 9.12 | 2.53 | 1.33 | 1.0 | 3.7 | 7.0 | 7.7 | 1.3 | 15.8 | 27.3 | 66.3 |
| physostigmine | 0.4 | 2.60 | 2.30 | 1.7 | 1.4 | 6.9 | 21.3 | 1.9 | 17.8 | 56.2 | 53.4 | mat and the time which it takes to decide to leave this position to explore the cage is recorded. After 20 seconds of exploration, the rat receives an electric shock (3 seconds duration) in the paws, causing a flight reaction. The rat is immediately removed from the apparatus and replaced in its original cage. In the course of the three subsequent tests (times: 4, 24 and 28 hours), the animal is replaced on the rubber mat and the time taken to leave this position is recorded. When the four paws of the animal rest on the grid, it receives an electric shock and is immediately removed from the apparatus.

At the start of the experiment, the rats are divided into 4 homogeneous groups of 15 animals. Thirty minutes before each test, each group of animals is subjected to a predetermined treatment:

group 1 receives an intraperitoneal injection of physiological salt solution;

group 2 receives an intraperitoneal injection of the compound to be tested;

group 3 receives an intraperitoneal injection of 0.5 mg scopolamine and group 4 receives an intraperitoneal injection of 0.5 mg scopolamine and an intraperitoneal injection of the compound to be tested, simultaneously.

Groups 1 and 2 are used in the first experiment and groups 3 and 4 are used in the second experiment.

The results obtained in this test with the compounds of the invention are summarized in Table V. This Table shows the number of the compound subjected to the test (column 1) and the dose administered intraperitoneally, expressed in mg/kg (column 2). Columns 3 and 4 show the results obtained in the test used to evaluate the learning. The figures indicate the average number of trials needed for a control animal (group 1) or an animal treated (group 2) with the compound to learn to remain on the rubber mat for 180 seconds in order to avoid the electric shock. The results were analyzed by the Student test. Columns 5 to 12 show the results obtained in the experiment used to evaluate the mnemic retention. In columns 5 to 8, the figures represent the average periods of remaining on the nat observed respectively at times 0, 4, 24 and 28 hours for the animals of group 3, treated only with scopolamine, and in columns 9 to 12 the corresponding figures for tne animals of groups 4, treated simultaneously with scopolamine and the compound studied (at the dose shown in the second column), are to be found.

From this Table, it can been seen that:

the compounds of the invention promote learning of the avoidance reflex: the average number of trials needed to reach the predetermined criterion (maximum period of remaining on the mat of 180 seconds) is lower for the treated animals (column 4) than for the control animals (column 3);

the amnesing effect of scopolamine is very pronounced: it can be seen that the period of remaining on the mat for the animals of group 3 (columns 5 to 8) are clearly less than the 180 seconds realized by the controls after an average number of trials (column 3): and under these conditions, the favorable influence of the compounds of the invention in counteracting the amnesing effect of scopolamine is very clear: the animals of group 4, treated simultaneously with scopolamine and with a compound of the invention, have periods of remaining on the mat at each observation which are considerably longer than those for the animals of group 3 treated with scopolamine alone (compare the results of column 5 with those of column 9, 6 with 10. etc.).

physostigmine exerts a favorable action against the amnesing effect of scopolamine, similar to that of the compounds of the invention but at a dose which has side effects and is very close to the toxic dose, which is not the case with the compounds of the invention.

5. Toxicity.

The toxicity of the c:xspounds of the invention has been determined on male NMRI mice by means of the Irwin's test (S. IRWIN, Psychopharmacologia,13,(1968),222–257). Progressive doses of the compound to be tested are administered intraperitoneally to groups of three mice until the lethal dose is reached (dose which causes the death of two animals out of three within 48 hours).

Table VI below gives the lethal dose observed for the compounds of the invention. The Table shows that the compounds of the invention have a very low toxicity, in contrast to physostigmine.

TABLE VI

| Compound | Lethal dose (in mg/kg) | Compound | Lethal dose (in mg/kg) |
|---|---|---|---|
| 1 | 802 | 23 | >1024 |
| 2 | 718 | 24 | 880 |
| 3 | 844 | 25a | 838 |
| 4 | 886 | 25b | 947 |
| 5 | 563 | 26 | 922 |
| 6 | 886 | 27 | 1133 |
| 7 | 886 | 28 | >1030 |
| 8 | 886 | 29 | 398 |
| 9 | 844 | 30 | 1125 |
| 10 | 844 | 31 | 511 |
| 11 | 892 | 32 | 1222 |
| 12 | 982 | 33 | 1132 |
| 13 | 934 | 34 | 1174 |
| 14 | >1073 | 35 | 401 |
| 15 | 1121 | 36 | 1174 |
| 16 | 844 | 37 | 928 |
| 17 | 844 | 38 | >1012 |
| 18 | 1007 | 39 | >1114 |
| 19 | 1031 | 40 | 1157 |
| 20 | 799 | 41 | 294 |
| 21a | 996 | 42 | >931 |
| 21b | 905 | 43 | 351 |
| 22 | 1091 | physostigmine | 0.82 |

6. Posology and adminstration.

The pharmaceutical compositions containing the compounds according to the invention may be administered orally, parenterally or rectally. The pharmaceutical compositions which can be used for oral adminstration may be solids or liquid, for example in the form of tablets (coated or non-coated), pills, dragees, gelatine capsules, solutions, syrups and the like. The composition which can be used for parenteral adminstration are the pharmaceutical forms known for this mode of adminstration, for example aqueous or oily solutions, suspensions or emulsions. For rectal adminstration, the compositions containing the compounds of the invention are generally in the form of suppositories. The pharmaceutical forms, such as injectable solutions, injectable suspensions, tablets, drops, suppositories and the like are prepared by the methods currently used by pharmacists. The pharmaceutical forms also comprise compositions which can deliver the active product in a progressive manner. The compounds of the invention are mixed with a solid or liquid, non-toxic pharmaceutically acceptable carrier, and optionally with a dispersing agent, a disintegrating agent, a stabilizing agent and the like. Sweetening agents, coloring agents and the like may also be added if appropriate. The percentage of active compound in the pharmaceutical compositions can vary within very wides limits according to the patient and the mode of administration, in particular according to the frequency of administration.

As regards the daily dosage, this can vary within a wide range of dosage units, for example from 0.1 to 2 g of active compound, depending upon the mode of administration. Thus, for example, the daily dosage may be from 0.25 to 0.75 g. preferably 0.5 g, one to three times per day, if the compound is administered in the form of a tablet.

A formulation for tablets is given below as a non-limiting example of a composition containing a compound of the formula I, which can be administered orally.

Compound 1 250 m
Methylcellulose (Methocel K4M) 200 mg .
Dry lactose 154 m
Aerosil 5 mg
Anhydrous citric acid 60 mg
Talc 11 mg
Magnesiumm stearate 20 mg

We claim:

1. A 2-amino-4-morpholino-6-propyl-1,3,5-triazine, including its optionally active isomers and racemic mixtures of the formula

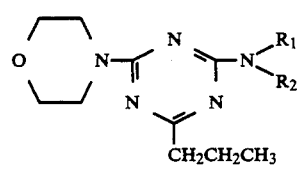

wherein
$R_1$ represents a hydrogen atom, an alkyl, phenylalkyl or acetyl radical,
$R_2$ represents a hydroxyl group, a hydroxyalkyl, alkoxyalkyl, dialkylamino, phenyl-hydroxyalkyl, (hydroxy-cycloalkyl)alkyl, alkanoyloxyalkyl, benzoyloxyalkyl, phenylacetyloxyalkyl or aminocarbonyloxyalkyl radical, a $COR_3$ group, in which $R_3$ represents an alkyl, phenyl, halophenyl, alkylphenyl, alkoxyphenyl, phenylalkyl or phenoxy radical, or a $CONR_4R_5$ group, in which $R_4$ and $R_5$ represent a hydrogen atom or alkyl radical, or,
$R_1$ and $R_2$, together with the nitrogen atom to which they are attached represent an alkyleneimino radical substituted by hydroxyalkyl radical, the above stated alkyl, alkoxy and alkanoyloxy radicals, either alone or as part of a more complex substituent, having 1 to 4 carbon atoms and the above stated cycloalkyl and alkyleneimino radicals having 4 to 6 carbon atoms, with the proviso that when $R_1$ represents the acetyl radical, $R_2$ represents an acetoxyalkyl radical, or a non-toxic pharmaceutically acceptable acid addition salt thereof.

2. A compound as claimed in claim 1, namely 2-[(4-morpholino-6-propyl-1,3,5-triazin-2-yl)amino]-ethanol or a non-toxic pharmaceutically acceptable salt thereof.

3. A compound as claimed in claim 1, namely 2-(hydroxyamino)-4-morpholino-6-propyl-1,3,5-triazine or a non-toxic pharmaceutically acceptable salt thereof.

4. A compound as claimed in claim 1, namely 2-[(2-methoxyethyl)amino]-4-morpholino-6-propyl-1,3,5-triazine or a non-toxic pharmaceutically acceptable salt thereof.

5. A compound as claimed in claim 1, namely (S)-3-[(4-morpholino-6-propyl-1,3,5-triazin-2-yl)amino]-2-propanol or a non-toxic pharmaceutically acceptable salt thereof.

6. A compound as claimed in claim 1, namely (R)-3-[(4-morpholino-6-propyl-1,3,5-triazin-2-yl)amino]-2-propanol or a non-toxic pharmaceutically acceptable salt thereof.

7. A compound as claimed in claim 1, namely 2-(2,2-dimethylhydrazino)-4-morpholino-6-propyl-1,3,5-triazine or a non-toxic pharmaceutically acceptable salt thereof.

8. A compound as claimed in claim 1, namely N-(4-morpholino-6-propyl-1,3,5-triazin-2-yl)-benzamide or a non-toxic pharmaceutically acceptable salt thereof.

9. A compound as claimed in claim 1, namely N-methyl-N-(4-morpholino-6-propyl-1,3,5-triazin-2-yl)-benzamide or a non-toxic pharmaceutically acceptable salt thereof.

10. A compound as claimed in claim 1, namely 2-[[2-acetoxy)ethyl]amino]-4-morpholino-6-propyl-1,3,5-triazine or a non-toxic pharmaceutically acceptable salt thereof.

11. A pharmaceutical composition comprising a therapeutically effective amount of a 2-amino-4-morpholino-6-propyl-1,3,5-triazine as claimed in claim 1 and a pharmaceutically acceptable solid or liquid diluent or carrier therefor.

12. A method for the treatment of cognitive and behavioral disorders associated with aging and with dementia syndromes in a patient in need thereof, which comprises administering to said patient an effective amount of a 2-amino-4-morpholino-6-propyl-1,3,5-triazine as claimed in claim 1.

* * * * *